(12) United States Patent
Brown

(10) Patent No.: US 11,172,988 B2
(45) Date of Patent: Nov. 16, 2021

(54) END FIRE FIBER ARRANGEMENTS WITH IMPROVED EROSION RESISTANCE

(71) Applicant: Joe Denton Brown, Panama City Beach, FL (US)

(72) Inventor: Joe Denton Brown, Panama City Beach, FL (US)

(73) Assignee: OPTICAL INTEGRITY, INC., Panama City Beach, FL (US)

( * ) Notice: Subject to any disclaimer, the term of this patent is extended or adjusted under 35 U.S.C. 154(b) by 337 days.

(21) Appl. No.: 15/417,934

(22) Filed: Jan. 27, 2017

(65) Prior Publication Data

US 2017/0209216 A1 Jul. 27, 2017

Related U.S. Application Data

(60) Provisional application No. 62/287,668, filed on Jan. 27, 2016.

(51) Int. Cl.
*A61B 18/22* (2006.01)
*A61B 18/24* (2006.01)
*G02B 6/26* (2006.01)
*A61B 18/00* (2006.01)

(52) U.S. Cl.
CPC ............ *A61B 18/24* (2013.01); *A61B 18/245* (2013.01); *G02B 6/262* (2013.01); *A61B 2018/00547* (2013.01); *A61B 2018/2205* (2013.01); *A61B 2018/2272* (2013.01)

(58) Field of Classification Search
CPC ............ A61B 18/22; A61B 2018/2205; A61B 2018/2244; A61B 2018/2255; A61B 18/24; A61B 18/245; A61B 2018/00315; A61B 2018/00345; A61B 2018/00404; A61B 2018/00505; A61B 2018/00511; A61B 2018/00517; A61B 2018/00547
USPC ............... 606/7, 13–16; 607/88, 89, 92, 93; 600/101, 104, 105, 108, 114
See application file for complete search history.

(56) References Cited

U.S. PATENT DOCUMENTS

| | | | | |
|---|---|---|---|---|
| 4,695,697 | A | * 9/1987 | Kosa | A61B 18/20 219/121.62 |
| 4,913,142 | A | 4/1990 | Kittrell | |
| 5,257,991 | A | 11/1993 | Fletcher et al. | |
| 5,631,986 | A | * 5/1997 | Frey | G02B 6/3835 385/78 |
| 5,649,923 | A | * 7/1997 | Gregory | A61B 18/24 606/14 |
| 5,693,043 | A | * 12/1997 | Kittrell | A61B 1/00096 606/15 |
| 7,226,444 | B1 | 6/2007 | Ellman | |

(Continued)

*Primary Examiner* — Ahmed M Farah
(74) *Attorney, Agent, or Firm* — Bacon & Thomas, PLLC

(57) ABSTRACT

A protective ferrule for an end-firing optical fiber arrangement combines a spherical or rounded shape with a planar end. The combination of the spherical or rounded shape and planar end provides protection for the working channel of an endoscope or catheter through which the fiber is inserted while confining and minimizing erosion of the active surface area of the fiber. The protective ferrule of may be fitted to the end of the optical fiber by the steps of heating the ferrule to expand an inside diameter so that it fits over the end of the fiber, with subsequent cooling of the ferrule causing it to contract and create a compression fit.

2 Claims, 1 Drawing Sheet

(56) References Cited

U.S. PATENT DOCUMENTS

| | | | |
|---|---|---|---|
| 8,425,500 B2* | 4/2013 | Hanley | A61B 18/24 29/426.2 |
| 8,864,755 B2* | 10/2014 | Appling | A61B 18/24 606/15 |
| 9,678,275 B1* | 6/2017 | Griffin | G02B 6/3624 |
| 2002/0188285 A1 | 12/2002 | Brown | |
| 2002/0193781 A1 | 12/2002 | Loeb | |
| 2005/0131400 A1* | 6/2005 | Hennings | A61B 18/24 606/15 |
| 2005/1031399 | 6/2005 | Loeb | |
| 2005/0154379 A1 | 7/2005 | McGowan, Sr. | |
| 2007/0270788 A1 | 11/2007 | Nahen et al. | |
| 2008/0188843 A1* | 8/2008 | Appling | A61B 18/24 606/15 |
| 2008/0195085 A1 | 8/2008 | Loeb | |
| 2009/0221994 A1* | 9/2009 | Neuberger | A61B 18/24 606/7 |
| 2009/0240242 A1* | 9/2009 | Neuberger | A61B 18/24 606/7 |
| 2000/9028719 | 11/2009 | Hanley | |
| 2013/0023729 A1* | 1/2013 | Vazales | A61B 1/0669 600/104 |
| 2013/0345686 A1* | 12/2013 | Brown | A61B 18/22 606/15 |

* cited by examiner

END FIRE FIBER ARRANGEMENTS WITH IMPROVED EROSION RESISTANCE

BACKGROUND OF THE INVENTION

1. Field of the Invention

This invention relates to optical fibers used in laser treatment applications such as, by way of example and not limitation, benign prostate hypertrophy (BPH) treatments.

The invention provides improvements to the end-fire optical fiber arrangement with improved erosion resistance described in the inventor's U.S. patent application Ser. No. 13/692,512, incorporated herein by reference, which was filed Dec. 3, 2012, and published as U.S. Pat. Publ. No. 2013/0345686.

According to one aspect, the invention modifies a protective ferrule of the end-firing optical fiber arrangement described in the inventor's U.S. patent application Ser. No. 13/692,512, by providing the protective ferrule that combines a spherical or rounded shape with a planar end. The combination of the spherical or rounded shape and planar end provides protection for the working channel of an endoscope or catheter through which the fiber is inserted while confining and minimizing erosion of the active surface area of the fiber.

According to another aspect, the protective ferrule of the end-firing optical fiber arrangement is fitted to the end of the optical fiber by the steps of heating the ferrule to expand an inside diameter so that it fits over the end of the fiber, with subsequent cooling of the ferrule causing it to contract and create a compression fit.

2. Description of Related Art

FIG. 1A shows a conventional optical fiber having a core 5 and cladding 1. End of the optical fiber is a polished flat tip 10.

FIG. 1B shows the same fiber as FIG. 1, but after laser interaction with a stone or tissue. The polished flat tip 10 of the fiber has now eroded to form an irregular surface 20 with sharp edges that could damage an endoscope's working channel.

FIG. 2A shows the arrangement disclosed in parent U.S. patent application Ser. No. 13/692,512, in which a ferrule 32 is welded to a fiber 15 to create end-firing fiber assembly 30. The end of the fiber assembly 30 is a polished flat or rounded surface 35. As described in U.S. patent application Ser. No. 13/692,512, the ferrule may be a quartz ferrule having an index of refraction that is matched to that of the fiber. In addition, the core 3 and cladding are illustrated as having an outward taper, i.e., the diameter of the fiber has been expanded in a radially outward direction towards the end surface 35, as described by Hutchens et al. in the article "Hollow Steel Tips for Reducing Distal Fiber Burn-Back During Thulium Fiber Laser Lithotripsy, *Journal of Biomedical Optics* 18(7), 078001 (July 2013).

Both the use of a quartz ferrule and outwardly tapered fiber illustrated in FIG. 2A have the effect of reducing erosion following interaction with a stone or tissue. Nevertheless, as illustrated in FIG. 2B, which shows laser assembly 30 following laser interaction with a stone or tissue, the eroded surface 36 is still sufficiently jagged to cause damage to the endoscope's working channel.

FIG. 3A shows a modification of the fiber shown in FIGS. 1A and 1B. In this arrangement, the fiber tip assembly 40 has a ball or spherical shape, forming a round surface with no edges to damage an endoscope, as described by Peter Kronenberg et al. in the article entitled "Lithotripsy Performance of Specially Designed Laser Fiber Tips," which was accepted for publication in *The Journal of Urology* on Oct. 25, 2015. Again, the core and cladding 3 have been expanded in a radially outward direction toward the tip of the fiber, i.e., outwardly tapered, so that the outer edge 7 of the fiber tip has an expanded diameter. Nevertheless, as illustrated in FIG. 3B, erosion of the fiber tip 40 can still result in a sharp or jagged eroded surface 46 with the potential to damage the working channel of the endoscope.

SUMMARY OF THE INVENTION

According to one aspect, the present invention further modifies the ferrule arrangement of FIGS. 2A and 2B and the ball tip arrangement of FIGS. 3A and 3B, by combining a ferrule having a rounded or spherical shape to protect the working channel of an endoscope with an optical fiber having an end surface that is substantially flat or planar rather than spherical.

According to this aspect of the present invention, the optical fiber itself does not need to be outwardly tapered. Instead, the outer diameter of the fiber is preferably not expanded, so as to limit the surface area that is eroded.

According to a second aspect of the present invention, a method of attaching a ferrule to the end of the fiber is provided that does not require welding, thereby simplifying assembly of the ferrule to the fiber. This is accomplished by first heating the ferrule so that it expands and its inner diameter is larger than the diameter of the fiber, at which time the expanded ferrule can easily be fitted over the end of the fiber. After the ferrule is positioned over the end of the fiber, the ferrule is permitted to cool so that the inner diameter of the ferrule shrinks to be equal to or slightly smaller than the diameter of the fiber, thus securing the ferrule to the fiber with a compression fit.

It will be appreciated by those skilled in the art that the two aspects of the invention are independent of each other, so that the rounded or spherical ferrule of the first aspect of the invention may be attached to a fiber by conventional welding or other methods than heating and cooling, and the heating/cooling method of the second aspect of the invention may be applied to ferrules having shapes other than a ball or rounded shape, including the cylindrical shape illustrated in FIGS. 2A and 2B.

DETAILED DESCRIPTION OF THE PREFERRED EMBODIMENTS

Figures 4A, 4B:
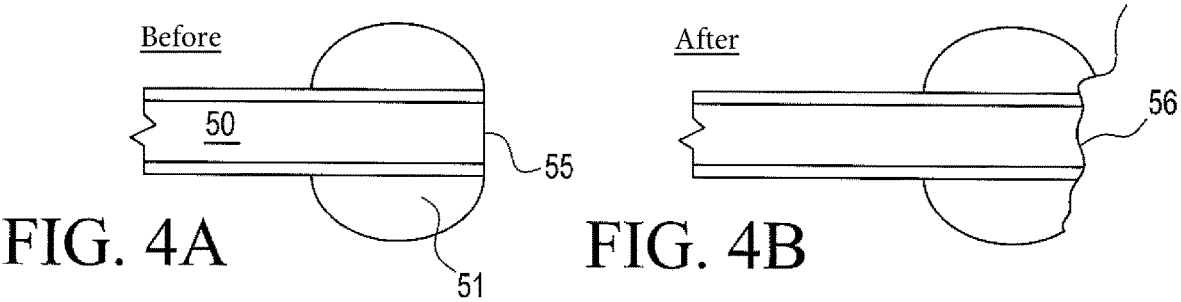
FIGS. 4A and 4B are side views of the end-firing optical fiber arrangement of a preferred embodiment of the invention, respectively taken before and after interaction with a stone or tissue.

FIGS. 4A and 4B show a preferred embodiment of the present invention that includes an end-firing optical fiber 50 and a ferrule 51 secured to the cladding at a distal end of the fiber.

As illustrated in FIG. 4A, the ferrule 51 has a generally spherical or rounded shape, but the end surface 55 is a generally flat or planar polished rather than a spherical surface. In addition, the fiber core and cladding have not been tapered or expanded in a radially outward direction, in contrast to the fibers shown in FIGS. 3A, 3B, 4A, and 4B. Instead, the diameter 11 of the core and cladding remains constant over the length of the fiber, including at the tip of the fiber. As in U.S. patent application Ser. No. 13/693,592, the ferrule 51 may be a quartz ferrule having an index of refraction matched to that of the fiber 10, so that laser energy disperses to increase the firing angle of the laser. Alternatively, the ferrule may be made of sapphire or another suitable material.

Figures 2A, 2B:
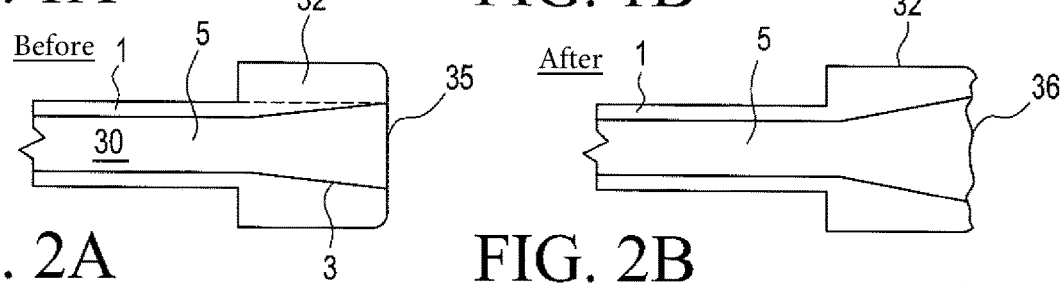
FIGS. 2A and 2B are side views of the ferrule-protected end-firing optical fiber assembly disclosed in U.S. patent application Ser. No. 13/692,512, respectively taken before and after laser interaction with a stone or tissue.
Figures 3A, 3B:
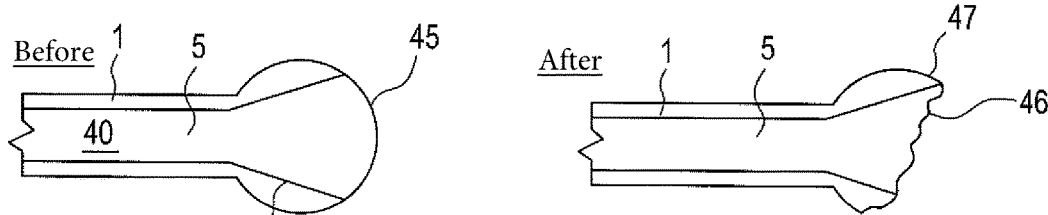
FIGS. 3A and 3B are side views of a conventional ball tip fiber arrangement, respectively taken before and after laser interaction with a stone or tissue.

As illustrated in FIG. 4B, in contrast to the situations shown in FIGS. 2B and 3B, the erosion is substantially limited to the active surface area 56 of the fiber end surface, while still leaving rounded edges to protect the endoscope. Furthermore, the rate of erosion will actually decrease with continued usage since the surface 56 stops making contact with the target stone or tissue, contact with the stone or tissue.

Figure 5A:
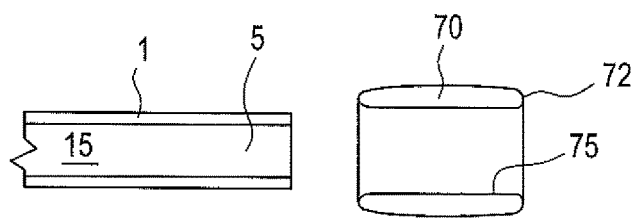
FIGS. 5 and 5B are side views illustrating two steps of a preferred method of assembling a protective ferrule to an optical fiber without welding.
Figure 5B:
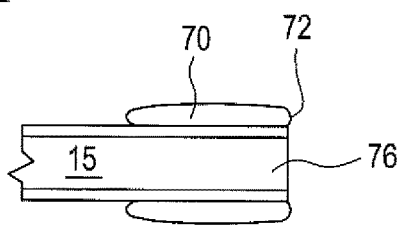

The method illustrated in FIGS. 5A and 5B begins with the step, shown in FIG. 5A, of heating the ferrule 70 so that it expands and the inner diameter 75 of the ferrule is larger than an outer diameter of the fiber 15. The ferrule 70 is then positioned relative to the fiber 15, so that fiber tip 26 is flush or slightly recessed with respect to the polished front surface 72 of the ferrule 70. At this time, the ferrule 70 is permitted to cool sufficiently to shrink and grip the fiber, creating a compression fit. As a result, there is no need to weld the ferrule to the fiber. A material for the ferrule that has appropriate thermal expansion properties is sapphire.

FIG. 3 shows variations of an end-firing fiber arrangement in accordance with a second preferred embodiment of the invention. In the arrangement indicated by reference numeral 20 of FIG. 3, a small, flexible, end-firing optical fiber 1 without an angled tip is fused to a quartz ferrule 6, and the fiber 1 and ferrule 6 are mounted in a pre-formed flexible cannula 2 whose unstressed shape is a curvature that causes the fiber end to point laterally and enable treatment radiation to be directed to tissues situated at the side of the fiber insertion axis. The flexible cannula 2 is preferably made of a shape memory material with sufficient flexibility to cause the cannula to straighten, as indicated by reference numeral 22, upon withdrawal or insertion into the straight working channel of a cystoscope or other scope or introducer (not shown), but that returns to the curved shape when extended out of the scope.

As a result of this arrangement, the material of the ferrule situated between the end of the fiber and the tissue, at which treatment radiation is directed, can be made as thick as desired while still permitting the treatment radiation to be directed at lateral tissues, and without affecting the ability of the fiber and ferrule to fit within the working channel of a standard cystoscope or other scope having a limited working channel diameter.

Reference numeral 24 indicates a close-up of the ferrule 5 in the arrangement indicated by reference numerals 20 and 22. As illustrated, the fuse length 6 can be adjusted along the ferrule length 15 to 6 mm or more, giving at least three times more erosion before a hole is formed, as compared to the 1.8 mm thickness limitation to which the side firing fiber and cap of the prior art is subject, as discussed above. The tip 15 of this example is flat polished, although a rounded tip may also be provided, as indicated by reference numeral 25.

As an alternative to the fused ferrule 5 of the arrangements indicated by reference numerals 20, 22, 24, and 25, a non-fused fiber and ferrule arrangement may be provided, as indicated by reference numeral 26. In this arrangement, the tip 12 of the non-fused ferrule 5 may be recessed to keep the tip from being sunk into prostate or other tissue being treated. Since the fiber 1 is not fused to the ferrule 5 in this example, the fiber can be extended into the ferrule as it is eroded, in a manner analogous to extension of the lead in a mechanical pencil, giving more life to the fiber over a given procedure.

Figures 1A, 1B:
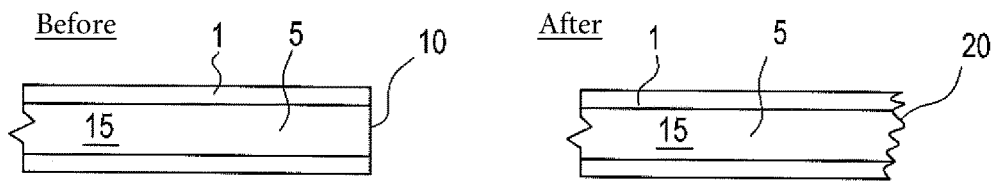
FIGS. 1A and 1B are side views of a conventional end-firing optical fiber, respectively taken before and after laser interaction with a stone or tissue during a surgical procedure.

FIG. 4 shows a variation of the non-fused arrangement of FIG. 1, in which a quartz ferrule 42 corresponding to ferrule 5 of FIG. 1 is secured to the cannula 2 and the fiber is free to be positioned within the ferrule, as indicated by arrow 40. In this variation, irrigation fluid 35, such as water, saline, or air, is permitted to enter the ferrule 42, and the fiber is capable of being moved forward or backwards to increase or decrease a power density of radiation incident on a tissue 50 positioned directly in front of the ferrule 42.

Having thus described preferred embodiments of the invention in connection with the accompanying drawings, it will be appreciated that the invention is not to be limited to the specific embodiments or variations disclosed.

I claim:

1. An end-firing surgical laser arrangement, comprising:
   an optical fiber configured to be inserted through a working channel of an endoscope or catheter, the optical fiber having a planar end face through which laser energy exits the optical fiber; and
   a protective ferrule fitted over an end of the optical fiber and having a spherical or rounded end,
   wherein the protective ferrule is configured to be inserted together with the optical fiber through the working channel of the endoscope, and surrounds the optical fiber while leaving exposed the planar end face of the optical fiber,
   wherein the planar end face of the optical fiber extends to and is flush with the spherical or rounded end of the protective ferrule, and
   whereby the spherical or rounded shape of the protective ferrule provides protection for the working channel of the endoscope or catheter through which the optical fiber is inserted while the planar end face of the optical fiber confines and minimizes erosion of an active surface area of the planar end face of the fiber.

2. The laser arrangement of claim 1, wherein the protective ferrule is compression fit to the end of the optical fiber.

* * * * *